US00PP13777P29

(12) United States Plant Patent
Zary

(10) Patent No.: US PP13,777 P2
(45) Date of Patent: May 6, 2003

(54) FLORIBUNDA ROSE PLANT NAMED 'JACTURPL'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/000,390

(22) Filed: Nov. 30, 2001

(51) Int. Cl.[7] ..... A01H 5/00
(52) U.S. Cl. ..... Plt./143
(58) Field of Search ..... Plt./143, 142, 141, Plt./102, 130, 132

*Primary Examiner*—Howard J. Locker
(74) *Attorney, Agent, or Firm*—Klarquist Sparkman, LLP

(57) ABSTRACT

Floribunda rose plant having a strong fragrance similar to a gardenia; long stems; strong, upright growth; dark green, glossy foliage; and rich near-purple, and white striped flowers.

1 Drawing Sheet

SUMMARY OF THE INVENTION

The present invention relates to a new and distinct variety of rose plant of the floribunda class which was originated by me by crossing the variety JACpurr (unpatented), with an unnamed seedling (unpatented).

BACKGROUND OF THE INVENTION

The primary objective of this breeding was to produce a new rose variety having rich purple and white striped flowers of the female parent and its strong fragrance combined with the plant vigor and long stems of the pink and white striped unnamed male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Strong fragrance similar to that of a gardenia;
2. Long stems;
3. Strong, upright growth;
4. Dark green, glossy foliage; and
5. Rich near purple, and white striped flowers.

Asexual reproduction of this new variety by budding, as performed at Wasco, Calif., shows that the foregoing and all other characteristics and distinctions come true to form and are established and transmitted through succeeding propagations.

COMPARISON WITH PARENTS

JACturpl differs from JACpurr in that it is a much taller plant and its flowers are not as deep a purple. It differs from the unnamed male parent in that it is much more fragrant and has a much deeper flower color.

COMPARISON WITH SIMILAR VARIETY

There is no other striped rose with the same flower color, plant vigor or fragrance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) colour chart, except where ordinary dictionary significance of color is indicated.

Parentage:
*Seed parent.*—JACpurr (unpatented).
*Pollen parent.*—Unnamed seedling (unpatented).
Classification:
*Botanical.*—*Rosa hybrida.*
*Commercial.*—Floribunda.

FLOWER

Observations made from plants beginning at 2 years of age grown in a garden environment at Somis, Calif. from January, 2000 to August, 2001.

Blooming habit: Continuous.
Bud:
*Size.*—28–34 mm long when the petals start to unfurl.
*Form.*—The bud form is long.
*Color.*—When sepals first divide, bud color is White Group 155D and Red-Purple Group 60C striped. When half blown, the upper sides of the petals are striped with Red-Purple Group 61B, Red-Purple Group 62B and White Group 155D; and the lower sides of the petals are striped with Red-Purple Group 63C and White Group 155D.
*Sepals.*—Color: Upper surface: Greyed-Purple Group 183C with Yellow-Green Group 145B at the base. Lower surface: Yellow-Green Group 144A. Length: 23–25 mm. Width: 9–10 mm. Shape: Subulate. Texture: Upper surface: Hoary. Lower surface: Glandular. There are three heavily appendaged sepals. There are two unappendaged sepals with hairy, glandular edges.

*Receptacle.*—Color: Yellow-Green Group 144A. Shape: Funnel. Size: Small, about 5 mm×3 mm. Surface: Hairy, glandular.

*Peduncle.*—Length: Medium, averaging about 5–7 cm. Surface: Glandular. Color: Yellow-Green Group 146C with anthocyanin of Greyed-Purple Group 183D. Strength: Stiff, erect.

Blooms:

*Size.*—Large. Average open size is 9–11 cm.

*Borne.*—Singly and in pyramidal clusters of 3–5 blooms, finishing flat.

*Stems.*—Strength: Strong. Average length is about 40–50 cm.

*Form.*—When first open: High centered. Permanence: Slight quill fashion; outer petal edges curl slightly.

*Petalage.*—Number of petals under normal conditions: 25.

*Color.*—The upper sides of the petals are a striping of Red-Purple Group 61B, Red-Purple Group 62B, and White Group 155D. The reverse sides of the petals are a striping of Red-Purple Group 63C and White Group 155D. The base of each petal is Yellow Group 7D. The major color on the upper side is Red-Purple Group 61B, Red-Purple Group 62B and White Group 155D.

*Discoloration.*—At the end of the third day: Red-Purple Group 61B, Red-Purple Group 62B and White Group 155D. By day 7, petals fade to Red-Purple Group 68A and White Group 155D.

*Fragrance.*—Strong. Character of fragrance: Sweet-Gardenia.

Petals:

*Texture.*—Thick.

*Shape.*—Round.

*Margin.*—Entire.

*Apex shape.*—Obtuse.

*Base shape.*—Rounded.

*Form.*—Tips slightly recurved, edges slightly quilled.

*Arrangement.*—Imbricated.

*Petaloids.*—Number: Few (3–5). Color: Red Group 68B and White Group 155D.

*Persistence.*—Petals drop off cleanly before drying.

*Lastingness.*—On the plant: Long (about 8–10 days). As a cut flower: Not tested.

Reproductive parts:

*Stamens.*—Number: 260–280. Length: 9–13 mm. Anthers: Length: 2–3 mm. Color: Yellow-Orange Group 21C. Arrangement: Regular around styles. Filaments: Color: Yellow Group 5D. Length: 7–10 mm. Pollen: Color: Yellow-Orange Group 20B.

*Pistils.*—Number: 110–130. Styles: Color: Orange-White Group 159D. Length: 4–5 mm. Stigmas: Color: Yellow-Group 8C.

*Hips.*—None observed.

Plant:

*Form.*—Bush.

*Growth.*—Vigorous, upright and branching.

*Mature plant.*—Height is 1.3–1.5 meters, width is 0.9–1.1 meters.

*Rootstock.*—Dr. Huey.

Foliage: Number of leaflets on normal mid-stem leaves: 5–7.

*Size.*—Large (12–13 cm long×8–9 cm wide).

*Quantity.*—Abundant.

*Color.*—New foliage: Upper side: Greyed-Purple Group 183A. Lower side: Greyed-Purple Group 183B. Old foliage: Upper side: Green Group 137A. Lower side: Yellow-Green Group 147B.

Leaflets:

*Size.*—Length: 4–6 cm. Width: 2.5–3.5 cm.

*Shape.*—Ovate.

*Base shape.*—Obtuse.

*Apex shape.*—Acuminate.

*Texture.*—Leathery, glossy.

*Edge.*—Serrated.

*Serrations.*—Single and small.

*Petiole color.*—Yellow-Green Group 146B.

*Petiole rachis.*—Color: Yellow-Green Group 146B.

*Petiole underside.*—Glandular with prickles. Yellow-Green Group 145B.

*Stipules.*—Long (about 25 mm) bearded and glandular.

*Disease resistance.*—Resistant to mildew and rust, susceptible to blackspot under normal growing conditions.

*Pest persistance.*—Not tested.

Wood:

*New wood.*—Color: Greyed-Purple Group 183A. Bark: Smooth.

*Old wood.*—Color: Yellow-Green Group 146B. Bark: Smooth.

Prickles:

*Quantity.*—On main canes from base: Few. On laterals from main canes: Few.

*Form.*—Hooked downward.

*Length.*—10 mm×10 mm.

*Color when young.*—Greyed-Orange Group 176A.

*Color when mature.*—Greyed-Orange Group 177A.

Small prickles: Quantity: On main stalks: None. On laterals: None.

Winter hardiness: Hardy to Zone 5.

I claim:

1. A new and distinct variety of rose plant of the floribunda class, substantially as herein shown and described, characterized particularly by strong fragrance similar to a gardenia; long stems; strong, upright growth; dark green, glossy foliage; and rich near-purple, and white striped flowers.

* * * * *

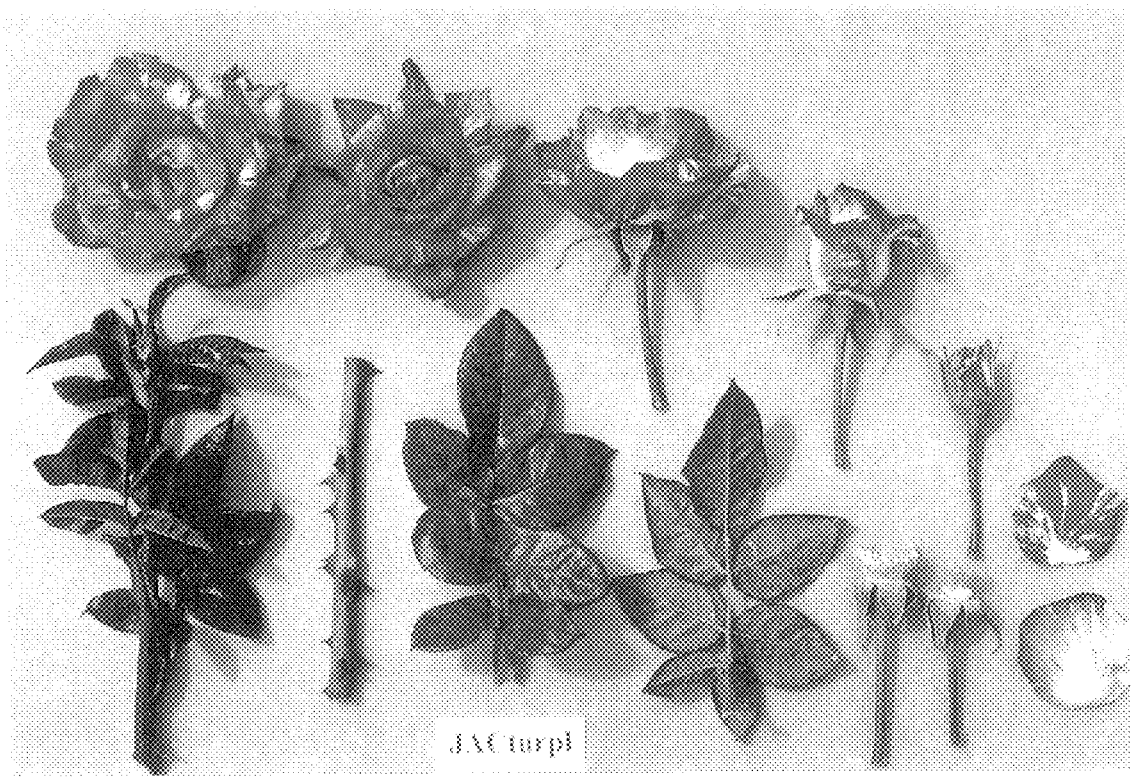
JAC turpl